(12) United States Patent
Inoue et al.

(10) Patent No.: US 7,713,972 B2
(45) Date of Patent: May 11, 2010

(54) IMIDAZOTRIAZINONE DERIVATIVES AS PDE 7 (PHOSPHODIESTERASE 7) INHIBITORS

(75) Inventors: Hidekazu Inoue, Osaka (JP); Hidenobu Murafuji, Osaka (JP); Yasuhiro Hayashi, Osaka (JP)

(73) Assignee: Asubio Pharma Co., Ltd., Tokyo (JP)

( * ) Notice: Subject to any disclaimer, the term of this patent is extended or adjusted under 35 U.S.C. 154(b) by 483 days.

(21) Appl. No.: 10/560,503

(22) PCT Filed: Jun. 11, 2004

(86) PCT No.: PCT/JP2004/008642

§ 371 (c)(1),
(2), (4) Date: Dec. 13, 2005

(87) PCT Pub. No.: WO2004/111053

PCT Pub. Date: Dec. 23, 2004

(65) Prior Publication Data

US 2006/0128707 A1    Jun. 15, 2006

(30) Foreign Application Priority Data

Jun. 13, 2003   (JP) .............................. 2003-170095

(51) Int. Cl.
| A61K 31/53 | (2006.01) |
| A01N 43/64 | (2006.01) |
| A01N 43/66 | (2006.01) |
| C07D 253/08 | (2006.01) |
| C07D 487/00 | (2006.01) |

(52) U.S. Cl. .......................... 514/243; 514/246; 544/183
(58) Field of Classification Search .................... None
See application file for complete search history.

(56) References Cited

U.S. PATENT DOCUMENTS

| 6,362,178 | B1 | 3/2002 | Niewohner et al. |
| 6,476,029 | B1 | 11/2002 | Niewohner et al. |
| 6,613,778 | B1 | 9/2003 | Eggenweiler et al. |
| 6,627,651 | B1 | 9/2003 | Shiraishi et al. |
| 6,737,436 | B1 | 5/2004 | Eggenweiler et al. |
| 2002/0198377 | A1 | 12/2002 | Niewohner et al. |
| 2004/0097498 | A1 | 5/2004 | Niewohner et al. |
| 2004/0138279 | A1 | 7/2004 | Eggenweiler et al. |
| 2005/0009822 | A1 | 1/2005 | Niewohner et al. |
| 2005/0043303 | A1 | 2/2005 | Niewohner |
| 2005/0195210 | A1 | 9/2005 | Demers et al. |

FOREIGN PATENT DOCUMENTS

| DE | 19950647 | 4/2001 |
| DE | 19962928 A1 * | 6/2001 |
| EP | 1 092 719 | 4/2001 |
| WO | WO 99/24433 | 5/1999 |
| WO | WO 99/67244 | 12/1999 |
| WO | WO 00/68203 | 11/2000 |
| WO | WO 01/32618 | 5/2001 |
| WO | WO 01/34601 | 5/2001 |
| WO | WO 01/47928 | 7/2001 |
| WO | WO 01/64677 | 9/2001 |
| WO | WO 01/74786 | 10/2001 |
| WO | WO 01/98274 | 12/2001 |
| WO | WO 02/28847 | 4/2002 |
| WO | WO 02/40450 | 5/2002 |
| WO | WO 02/50078 | 6/2002 |
| WO | WO 02/064593 | 8/2002 |
| WO | WO 02/068423 | 9/2002 |
| WO | WO 02/074754 | 9/2002 |
| WO | WO 02/074774 | 9/2002 |

(Continued)

OTHER PUBLICATIONS

Vippagunta, et. al.; Crystalline Solids, Advanced Drug Delivery Reviews; 48; 2001; 3-26.*

(Continued)

Primary Examiner—James O Wilson
Assistant Examiner—Jeffrey H Murray
(74) Attorney, Agent, or Firm—Hunton & Williams LLP

(57) ABSTRACT

The present invention provides the compounds inhibiting PDE 7 selectively, and therefore, enhances cellular cAMP level. Consequently, the compound is useful for treating various kinds of disease such as allergic disease, inflammatory disease or immunologic disease. The compound is imidazotriazinone compound represented by the following formula (IA) or (IB): especially, R1 is cyclohexyl group, R2 is methyl group; R3 is a hydrogen atom; nitro group; cyano group; a halogen atom; heteroaryl group; substituted or unsubstituted C1-C6 alkyl group; substituted or unsubstituted C2-C6 alkenyl group; saturated or unsaturated heterocycloalkyl group which is substituted or unsubstituted; a group: —NR5R6, —C(O)R7, —SO2R7, —OR8, —NR8COR7, —NR8SO2R7; A is CR4; and B is CH.

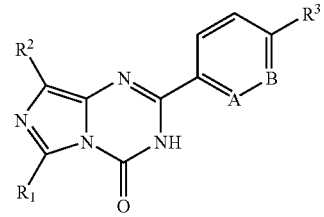

(IA)

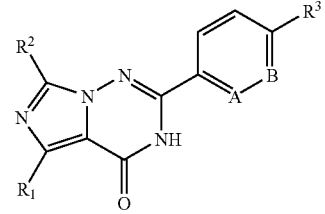

(IB)

24 Claims, No Drawings

FOREIGN PATENT DOCUMENTS

| | | |
|---|---|---|
| WO | WO 02/079203 | 10/2002 |
| WO | WO 02/087513 | 11/2002 |
| WO | WO 02/088080 | 11/2002 |
| WO | WO 02/098873 | 12/2002 |
| WO | WO 02/098879 | 12/2002 |
| WO | WO 02/098880 | 12/2002 |
| WO | WO 02/102315 | 12/2002 |
| WO | WO 03/011262 | 2/2003 |
| WO | WO 03/097645 | 11/2003 |

OTHER PUBLICATIONS

Dorwald F. A. Side Reactions in Organic Synthesis, 2005, Wiley: VCH, Weinheim p. IX of Preface.*

Vippagunta et. al. Advanced Drug Delivery Reviews 48 (2001) 3-26.*

Barnes et al. "Synthesis and Structure-Activity Relationships of Guanine Analogues as Phosphodiesterase 7 (PDE7) Inhibitors." Bioorg. Med. Chem. Lett. (2001), vol. 11, pp. 1081-1083.

Martinez et al. "Benzyl Derivatives of 2,1,3-Benzo- and Benzothieno[3,2-a]thiadiazine 2,2-Dioxides: First Phosphodiesterase 7 Inhibitors." J. Med. Chem. (2000), vol. 43, pp. 683-689.

Castro et al. "CoMFA of benzyl derivatives of 2,1,3-benzo and benzothieno[3,2-a]thiadiazine 2,2-dioxides: clues for the design of phosphodiesterase 7 inhibitors." Eur. J. Med. Chem. (2001), vol. 36, pp. 333-338.

International Preliminary Report on Patentability for International Application No. PCT/JP2004/008642, Dec. 29, 2005.

* cited by examiner

IMIDAZOTRIAZINONE DERIVATIVES AS PDE 7 (PHOSPHODIESTERASE 7) INHIBITORS

CROSS-REFERENCE TO RELATED APPLICATIONS

This application is a U.S. national stage application of International Application No. PCT/JP2004/008642, filed on Jun. 11, 2004, which claims the benefit of Japanese Patent Application No. 2003-170095, filed Jun. 13, 2003. All of the above applications are herein incorporated by reference in their entireties.

TECHNICAL FIELD

The present invention relates to imidazotriazinone compounds, pharmaceutically acceptable salts and solvates thereof, having PDE 7 (phosphodiesterase VII) inhibiting effect. These compounds are effective compounds for treating various kinds of disease such as allergic disease, inflammatory disease and immunologic disease.

BACKGROUND ART

A cyclic AMP (cAMP) or cyclic GMP (cGMP), which is an intracellular second messenger substance, is decomposed and inactivated by phosphodiesterase (PDE 1 to PDE 11). The PDE 7 selectively decomposes cAMP, and is characterized as an enzyme not decomposed by rolipram. Rolipram is a selective inhibitor of PDE 4 which decomposes cAMP.

It is suggested that PDE 7 plays an important role for activating T cells (Beavo, et al., *Science*, 283, 848 (1999)), and well known that activating of T-cell is concerned with the exacerbation of allergic disease, inflammatory disease or immunologic disease. These diseases are for example, bronchial asthma, chronic bronchitis, chronic obstructive pulmonary disease, allergic rhinitis, psoriasis, atopic dermatitis, conjunctivitis, osteoarthritis, rheumatoid arthritis, multiple sclerosis, systemic lupus erythematosus, inflammatory bowel disease, hepatitis, pancreatitis, encephalomyelitis, septicemia, Crohn's disease, rejection for organ transplantation, graft versus host disease (GVH disease), and restenosis after angioplasty. [*J. Allergy Clin. Immunol.*, 2000 November; 106 (5 Suppl.): S221-6; *Am. J. Respir. Crit. Care Med.*, 1996 February; 153(2): 629-32; *Am. J. Respir. Crit. Care Med.*, 1999 November; 160 (5 Pt 2): S33-7; *Clin. Exp. Allergy*, 2000 February; 30(2): 242-54; *Hosp. Med.*, 1998 July; 59(7): 530-3; *Int. Arch. Allergy Immunol.*, 1998 March; 115(3): 179-90; *J. Immunol.*, 1991 February 15; 146(4): 1169-74; *Osteoarthritis Cartilage*, 1999 July; 7(4): 401-2; *Rheum. Dis. Clin. North Am.*, 2001 May; 27(2): 317-34; *J. Autoimmun.*, 2001 May; 16(3): 187-92; *Curr. Rheumatol. Rep.*, 2000 February; 2(1): 24-31; *Trends Immunol.*, 2001 January; 22 (1): 21-6; *Curr. Opin. Immunol.*, 2000 August; 12(4): 403-8; *Diabetes Care*, 2001 September; 24(9): 1661-7; *J. Neuroimmunol.*, 2000 Nov. 1; 111 (1-2): 224-8; *Curr. Opin. Immunol.*, 1997 December; 9(6): 793-9; *JAMA*, 1999 September 15; 282 (11) :1076-82; *Semin. Cancer Biol.*, 1996 April; 7 (2): 57-64; *J. Interferon Cytokine Res.*, 2001 April; 21(4): 219-21].

Therefore, it is considered that a compound having PDE 7 inhibiting effect is useful for treating various kinds of disease such as allergic disease, inflammatory disease or immunologic disease concerned with T cells.

There has been proposed many compounds selectively inhibit PDE 7. These are for example, imidazopyridine derivatives (International Patent Publication WO 01/34601), dihydropurine derivatives (International Patent Publication WO 00/68203), pyrrole derivatives (International Patent Publication WO 01/32618), benzothiopyranoimidazolone derivatives (DE Patent 19950647), heterocyclic compounds (International Patent Publications WO 02/88080; 02/87513), quinazoline and pyridopyrimidine derivatives (International Patent Publication WO 02/102315), spiro tricyclic compounds (International Patent Publication WO 02/74754), thiazole and oxathiazole derivatives (International Patent Publication WO 02/28847), sulfonamide derivatives (International Patent Publication WO 01/98274), heterobiarylsulfonamide derivatives (International Patent Publication WO 01/74786), dihydroisoquinoline derivatives (International Patent Publication WO 02/40450), guanine derivatives (*Bioorg. Med. Chem. Lett.*, 11(2001), 1081), benzothiadiazine derivatives (*J. Med. Chem.*, 43 (2000), 683) and benzothienothiadiazine derivatives (*Eur. J. Med. Chem.*, 36(2001), 333). However, no curative medicines having PDE 7 inhibiting effect as main pharmacological mechanism have developed up to now.

Though some imidazotriazinone derivatives have been known (For examples: International Patent Publications WO 01/47928; WO 02/98880; WO 02/98879; WO 02/98873; WO 02/79203; WO 02/74774; WO 02/68423; WO 02/64593; WO 02/50078; WO 01/64677; WO 99/67244; WO 99/24433; and EP 1092719), the compounds represented by the general formula of the present application in which $R^1$ is cycloalkyl group or tert-butyl group have never been proposed and there is no suggestions that these compounds have PDE 7 inhibiting effect.

Therefore, the purpose of the present invention is to provide novel compounds having PDE 7 inhibiting effect, and PDE 7 inhibiting composition containing the same as an active ingredient.

The compounds of the present invention inhibit PDE 7 selectively, and therefore, enhance cellular cAMP level. Consequently, the compounds of the present invention are useful for treating various kinds of disease such as allergic disease, inflammatory disease or immunologic disease. For example, the compounds of the present invention are useful for treating or preventing the diseases such as bronchial asthma, chronic bronchitis, chronic obstructive pulmonary disease, allergic rhinitis, psoriasis, atopic dermatitis, conjunctivitis, osteoarthritis, rheumatoid arthritis, multiple sclerosis, systemic lupus erythematosus, inflammatory bowel disease, hepatitis, pancreatitis, encephalomyelitis, septicemia, Crohn's disease, rejection for organ transplantation, GVH disease, and restenosis after angioplasty.

DISCLOSURE OF INVENTION

Through extensive investigations of researching compounds having the capabilities of inhibiting PDE 7, the present inventors discovered that the compounds having imidazotriazinone skeleton in the molecular represented by the formula (IA) or (IB) mentioned below possess potent and selective PDE 7 inhibiting effect, and therefore, completed the present invention.

Accordingly, as one aspect of the present invention, it is provided imidazotriazinone compounds represented by the following formula (IA) or (IB):

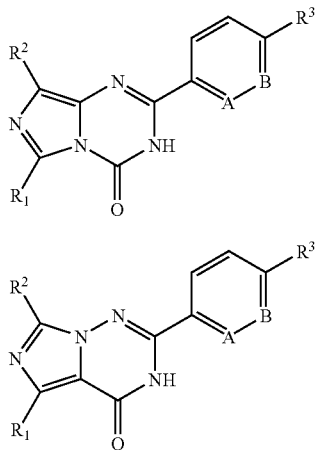

wherein:

A is N or CR$^4$;

B is N or CH;

R$^1$ is substituted or unsubstituted C$_3$-C$_8$ cycloalkyl group or tert-butyl group;

R$^2$ is a hydrogen atom or C$_1$-C$_6$ alkyl group;

R$^3$ is a hydrogen atom; nitro group; cyano group; a halogen atom; heteroaryl group; substituted or unsubstituted C$_1$-C$_6$ alkyl group; substituted or unsubstituted C$_2$-C$_6$ alkenyl group; saturated or unsaturated heterocycloalkyl group which is substituted or unsubstituted; a group: —NR$^5$R$^6$, —C(O)R$^7$, —SO$_2$R$^7$, —OR$^8$, —NR$^8$COR$^7$, —NR$^8$SO$_2$R$^7$;

R$^4$ is a hydrogen atom or C$_1$-C$_3$ alkoxy group which is unsubstituted or substituted by one or more fluorine atom(s);

R$^5$ and R$^6$ are, same or different from each other, a hydrogen atom; substituted or unsubstituted C$_1$-C$_6$ alkyl group; substituted or unsubstituted acyl group; or substituted or unsubstituted heterocycloalkyl group;

R$^7$ is a hydrogen atom; substituted or unsubstituted C$_1$-C$_6$ alkyl group; substituted or unsubstituted heterocycloalkyl group; OH; —OR$^8$ or —NR$^5$R$^6$;

R$^8$ is a hydrogen atom, substituted or unsubstituted C$_1$-C$_6$ alkyl group; or substituted or unsubstituted heterocycloalkyl group; or pharmaceutically acceptable salts or solvates thereof.

Still another aspect of the present invention, it is provided PDE 7 inhibiting composition containing the imidazotriazinone compounds mentioned above, or pharmaceutically acceptable salts or solvates thereof as an active ingredient.

BEST MODE FOR CARRYING OUT THE INVENTION

The present invention will now be explained more specifically as following.

The term "C$_1$-C$_6$ alkyl group" of the present invention includes a straight or branched-chained alkyl group having 1 to 6 carbon atoms, and the term "C$_2$-C$_6$ alkenyl group" of the present invention means a straight or branched-chained alkenyl group having 2 to 6 carbon atoms. The term "cycloalkyl group" of the present invention includes a cycloalkyl group having 3 to 8 carbon atoms such as cyclopropyl, cyclobutyl, cyclopentyl, cyclohexyl, cycloheptyl, and cyclooctyl.

The term "heterocycloalkyl group" is 3 to 7 membered heterocyclic group containing the same or different 1 to 4 hetero atom(s) such as oxygen, nitrogen or sulfur atom(s), and examples may include piperidinyl, pyrrolidinyl, piperazinyl, tetrahydrofuryl, tetrahydropyranyl, morpholinyl, azetidinyl, and homopiperazinyl.

The term "heteroaryl group" is 5 to 7 membered monocyclicorpolycyclic group thereof containing 2 to 8 carbon atoms and the same or different 1 to 4 hetero atom(s) such as oxygen, nitrogen or sulfur atom(s). The examples include pyrrole, furyl, thienyl, imidazolyl, thiazolyl, pyrazinyl, indolyl, quinolinyl, isoquinolinyl, tetrazolyl, pyridinyl, pyrazolyl, pyridazinyl, and pyrimidinyl. The "halogen atom" includes fluorine, chlorine, bromine and iodine.

Examples of the suitable substituent of "substituted or unsubstituted C$_1$-C$_6$ alkyl group", "substituted or unsubstituted C$_3$-C$_8$ cycloalkyl group", "substituted or unsubstituted alkenyl group", "substituted or unsubstituted heterocycloalkyl group" and "substituted or unsubstituted acyl group" include a straight or branched-chained, or substituted or unsubstituted alkyl group such as methyl, ethyl, propyl, isopropyl, n-butyl, tert-butyl, substituted or unsubstituted cycloalkyl group such as cyclopropyl, cyclobutyl, cyclopentyl, cyclohexyl, and cycloheptyl; hydroxyl group; cyano group; alkoxy group such as methoxy and ethoxy; substituted or unsubstituted amino group such as amino, methylamino, ethylamino, and dimethylamino; substituted or unsubstituted acyl group such as acetyl, and propionyl; substituted or unsubstituted aryl group; substituted or unsubstituted heteroaryl group; saturated or unsaturated heterocycloalkyl group which is substituted or unsubstituted; substituted or unsubstituted carbamoyl group; substituted or unsubstituted amide group; halogen atom; nitro group; substituted or unsubstituted sulfone group; oxo group; urea group; a straight or branched-chained, or cyclic alkenyl group which is substituted or unsubstituted such as ethenyl, propenyl, cyclohexenyl and the like.

The compounds wherein R$^1$ is cyclopentyl, cyclohexyl or cycloheptyl group; R$^2$ is methyl group; R$^3$ is hydrogen atom, halogen atom, heteroaryl group, C$_1$-C$_6$ alkyl group which is substituted or unsubstituted; C$_2$-C$_6$ alkenyl group which is substituted or unsubstituted, saturated or unsaturated heterocycloalkyl group which is substituted or unsubstituted; group —NR$^5$R$^6$ in which R$^5$R$^6$ is heterocycloalkyl group which is substituted or unsubstituted; A is CR$^4$ in which R$^4$ is methoxy or ethoxy group; and B is CH, are preferable out of the compounds represented by the formula (IA) or (IB).

The compounds of the formula (IA) and (IB) of the present invention may exist in the tautomeric mixtures, the tautomeric isomers per se, and the mixture thereof. Furthermore, the radiolabelled compounds of the formula (IA) and (IB) shall be included within the scope of the compounds of the present invention.

The compounds of the present invention contain one or more asymmetric carbon atom and therefore, the compounds of the present invention exist as optical isomer of (R)-form or (S)-form, racemic form, as well as diastereomers. Further, the compounds of the present invention exist as geometrical isomer such as (Z)-form or (E)-form due to the double bond in the substituent. Therefore, the compounds of the present invention should include these isomers per se as well as the isomeric mixtures thereof.

The compounds of the present invention may form acid additional salt thereof with various acids. Examples of the acid additional salt include the salts with inorganic acid such as hydrochloric acid, hydrobromic acid, hydriodic acid, sulfuric acid, nitric acid, phosphoric acid, and the like; salts with organic acid such as formic acid, acetic acid, propionic acid, oxalic acid, malonic acid, succinic acid, fumaric acid, maleic acid, lactic acid, malic acid, citric acid, tartaric acid, benzoic acid, picric acid, methanesulfonic acid, toluenesulfonic acid, benzenesulfonic acid, trichloroacetic acid, trifluoroacetic acid, asparaginic acid, glutamic acid and the like.

The compounds of the present invention may form pharmaceutically acceptable metal salts by treating with various kinds of metal, especially alkali metal or alkali earth metal. These salts may include sodium salt, potassium salt, calcium salt and the like. Further, the compounds of the present invention may include hydrate or solvate with water, ethanol or isopropanol, and polymorphisms thereof.

The following compounds are preferable imidazotriazinone compounds of the formula (IA) or (IB) of the present invention.

6-cyclohexyl-2-(2-methoxyphenyl)-8-methylimidazo[1,5-a][1,3,5]-triazin-4(3H)-one;
6-cyclohexyl-2-[2-methoxy-4-(1-piperazinyl)phenyl]-8-methylimidazo-[1,5-a][1,3,5]triazin-4(3H)-one;
6-cyclohexyl-2-[2-methoxy-4-(4-methyl-1-piperazinyl)phenyl]-8-methylimidazo[1,5-a][1,3,5]triazin-4(3H)-one;
2-[4-(4-amino-1-piperidinyl)-2-methoxyphenyl]-6-cyclohexyl-8-methylimidazo[1,5-a][1,3,5]triazin-4(3H)-one;
6-cyclohexyl-2-{2-methoxy-4-[4-(methylamino)-1-piperidinyl]phenyl}-8-methylimidazo[1,5-a][1,3,5]triazin-4(3H)-one;
6-cyclohexyl-2-{4-[4-(dimethylamino)-1-piperidinyl]-2-methoxy-phenyl}-8-methylimidazo[1,5-a][1,3,5]triazin-4(3H)-one;
6-cyclohexyl-2-[4-(1,4-diazepan-1-yl)-2-methoxyphenyl]-8-methylimidazo[1,5-a][1,3,5]triazin-4(3H)-one;
6-cyclohexyl-2-[2-methoxy-4-(4-methyl-1,4-diazepan-1-yl)phenyl]-8-methylimidazo[1,5-a][1,3,5]triazin-4(3H)-one;
6-cyclohexyl-2-[4-(4-hydroxy-1-piperidinyl)-2-methoxyphenyl]-8-methylimidazo[1,5-a)][1,3,5]triazin-4(3H)-one;
6-cyclohexyl-2-{4-[(4-hydroxy-1-piperidinyl)sulfonyl]-2-methoxyphenyl}-8-methylimidazo[1,5-a][1,3,5]triazin-4(3H)-one;
6-cyclohexyl-2-[2-methoxy-4-(1-piperazinylsulfonyl)phenyl]-8-methylimidazo[1,5-a][1,3,5]triazin-4 (3H)-one;
6-cyclohexyl-2-{2-methoxy-4-[(4-methyl-1-piperazinyl)sulfonyl]-phenyl}-8-methylimidazo[1,5-a][1,3,5]triazin-4(3H)-one;
6-cyclohexyl-2-[4-(1,4-diazepan-1-ylsulfonyl)-2-methoxyphenyl]-8-methylimidazo[1,5-a][1,3,5]triazin-4(3H)-one;
6-cyclohexyl-2-{2-methoxy-4-[(4-methyl-1,4-diazepam-1-yl) sulfonyl]-phenyl}-8-methylimidazo[1,5-a][1,3,5]triazin-4(3H)-one;
5-cyclohexyl-2-(2-methoxyphenyl)-7-methylimidazo[5,1-f][1,2,4]-triazin-4(3H)-one;
5-cyclohexyl-2-[2-methoxy-4-(4-methyl-1-piperazinyl)phenyl]-7-methylimidazo[5,1-f][1,2,4]triazin-4(3H)-one;
5-cyclohexyl-2-[2-methoxy-4-(1-piperazinyl)phenyl]-7-methylimidazo-[5,1-f][1,2,4]triazin-4(3H)-one;
2-[4-(4-amino-1-piperidinyl)-2-methoxyphenyl]-5-cyclohexyl-7-methylimidazo[5,1-f][1,2,4]triazin-4(3H)-one;
5-cyclohexyl-2-{2-methoxy-4-[4-(methylamino)-1-piperidinyl]phenyl}-7-methylimidazo[5,1-f][1,2,4]triazin-4(3H)-one;
5-cyclohexyl-2-{4-[4-(dimethylamino)-1-piperidinyl]-2-methoxy-phenyl}-7-methylimidazo[5,1-f][1,2,4]triazin-4(3H)-one;
5-cyclohexyl-2-[4-(1,4-diazepan-1-yl)-2-methoxyphenyl]-7-methylimidazo[5,1-f][1,2,4]triazin-4(3H)-one;

5-cyclohexyl-2-[2-methoxy-4-(4-methyl-1,4-diazepan-1-yl)phenyl]-7-methylimidazo[5,1-f][1,2,4]triazin-4(3H)-one;
5-cyclohexyl-2-[4-(4-hydroxy-1-piperidinyl)-2-methoxyphenyl]-7-methylimidazo[5,1-f][1,2,4]triazin-4(3H)-one;
5-cyclohexyl-2-{4-[(4-hydroxy-1-piperidinyl) sulfonyl]-2-methoxy-phenyl}-7-methylimidazo[5,1-f][1,2,4]triazin-4(3H)-one;
5-cyclohexyl-2-[2-methoxy-4-(1-piperazinylsulfonyl) phenyl]-7-methylimidazo[5,1-f][1,2,4]triazin-4(3H)-one;]
5-cyclohexyl-2-{2-methoxy-4-[(4-methyl-1-piperazinyl)sulfonyl]-phenyl}-7-methylimidazo[5,1-f][1,2,4]triazin-4(3H)-one;
5-cyclohexyl-2-[4-(1,4-diazepan-1-ylsulfonyl)-2-methoxyphenyl]-7-methylimidazo[5,1-f][1,2,4]triazin-4(3H)-one;
5-cyclohexyl-2-{2-methoxy-4-[(4-methyl-1,4-diazepan-1-yl)sulfonyl]-phenyl}-7-methylimidazo[5,1-f][1,2,4]triazin-4(3H)-one;
6-cyclohexyl-2-(2-ethoxyphenyl)-8-methylimidazo[1,5-a][1,3,5]-triazin-4(3H)-one;
6-cyclohexyl-2-[2-ethoxy-4-(1-piperazinyl)phenyl]-8-methylimidazo-[1,5-a][1,3,5]triazin-4(3H)-one;
6-cyclohexyl-2-[2-ethoxy-4-(4-methyl-1-piperazinyl)phenyl]-8-methylimidazo[1,5-a][1,3,5]triazin-4(3H)-one;
2-[4-(4-amino-1-piperidinyl)-2-ethoxyphenyl]-6-cyclohexyl-8-methylimidazo[1,5-a][1,3,5]triazin-4(3H)-one;
6-cyclohexyl-2-{2-ethoxy[4-(methylamino)-1-piperidinyl]phenyl}-8-methylimidazo[1,5-a][1,3,5]triazin-4(3H)-one;
6-cyclohexyl-2-{4-[4-(dimethylamino)-1-piperidinyl]-2-ethoxy-phenyl}-8-methylimidazo[1,5-a]([1,3,5]triazin-4(3H)-one;
6-cyclohexyl-2-[4-(1,4-diazepan-1-yl)-2-ethoxyphenyl]-8-methyl-imidazo[1,5-a][1,3,5]triazin-4(3H)-one;
6-cyclohexyl-2-[2-ethoxy-4-(4-methyl-1,4-diazepan-1-yl)phenyl]-8-methylimidazo[1,5-a][1,3,5]triazin-4 (3H)-one;
6-cyclohexyl-2-[4-(4-hydroxy-1-piperidinyl)-2-ethoxyphenyl]-8-methylimidazo[1,5-a][1,3,5]triazin-4(3H)-one;
6-cyclohexyl-2-{4-[(4-hydroxy-1-piperidinyl)sulfonyl]-2-ethoxy-phenyl}-8-methylimidazo[1,5-a][1,3,5]triazin-4(3H)-one;
6-cyclohexyl-2-[2-ethoxy-4-(1-piperazinylsulfonyl)phenyl]-8-methylimidazo[1,5-a][1,3,5]triazin-4(3H)-one;
6-cyclohexyl-2-{2-ethoxy-4-[(4-methyl-1-piperazinyl)sulfonyl]-phenyl}-8-methylimidazo[1,5-a][1,3,5]triazin-4(3H)-one;
6-cyclohexyl-2-[4-(1,4-diazepan-1-ylsulfonyl)-2-ethoxyphenyl]-8-methylimidazo[1,5-a][1,3,5]triazin-4(3H)-one;
6-cyclohexyl-2-{2-ethoxy-4-[(4-methyl-1,4-diazepan-1-yl)sulfonyl]-phenyl}-8-methylimidazo[1,5-a][1,3,5]triazin-4(3H)-one;
5-cyclohexyl-2-(2-ethoxyphenyl)-7-methylimidazo[5,1-f][1,2,4]-triazin-4(3H)-one;
5-cyclohexyl-2-[2-ethoxy-4-(4-methyl-1-piperazinyl)phenyl]-7-methylimidazo[5,1-f][1,2,4]triazin-4(3H)-one;
5-cyclohexyl-2-[2-ethoxy-4-(1-piperazinyl)phenyl]-7-methyl-imidazo[5,1-f][1,2,4]triazin-4(3H)-one;
2-[4-(4-amino-1-piperidinyl)-2-ethoxyphenyl]-5-cyclohexyl-7-methylimidazo[5,1-f][1,2,4]triazin-4(3H)-one;
5-cyclohexyl-2-{2-ethoxy-4-[4-(methylamino)-1-piperidinyl]phenyl}-7-methylimidazo[5,1-f][1,2,4]triazin-4(3H)-one;

5-cyclohexyl-2-{4-[4-(dimethylamino)-1-piperidinyl]-2-ethoxy-phenyl}-7-methylimidazo[5,1-f][1,2,4]triazin-4(3H)-one;

5-cyclohexyl-2-[4-(1,4-diazepan-1-yl)-2-ethoxyphenyl]-7-methyl-imidazo[5,1-f][1,2,4]triazin-4(3H)-one;

5-cyclohexyl-2-[2-ethoxy-4-(4-methyl-1,4-diazepan-1-yl)phenyl]-7-methylimidazo[5,1-f][1,2,4]triazin-4(3H)-one;

5-cyclohexyl-2-[4-(4-hydroxy-1-piperidinyl)-2-ethoxyphenyl]-7-methylimidazo[5,1-f][1,2,4]triazin-4(3H)-one;

5-cyclohexyl-2-{4-[(4-hydroxy-1-piperidinyl)sulfonyl]-2-ethoxyphenyl}-7-methylimidazo[5,1-f][1,2,4]triazin-4(3H)-one;

5-cyclohexyl-2-[2-ethoxy-4-(1-piperazinylsulfonyl)phenyl]-7-methylimidazo[5,1-f][1,2,4]triazin-4(3H)-one;

5-cyclohexyl-2-{2-ethoxy-4-[(4-methyl-1-piperazinyl) sulfonyl]-phenyl}-7-methylimidazo[5,1-f][1,2,4]triazin-4(3H)-one;

5-cyclohexyl-2-[4-(1,4-diazepan-1-ylsulfonyl)-2-ethoxyphenyl]-7-methylimidazo[5,1-f][1,2,4]triazin-4(3H)-one;

5-cyclohexyl-2-{2-ethoxy-4-[(4-methyl-1,4-diazepan-1-yl)sulfonyl]-phenyl}-7-methylimidazo[5,1-f][1,2,4]triazin-4(3H)-one.

The compound of the formula (IA) of the present invention can be synthesized by the following methods.

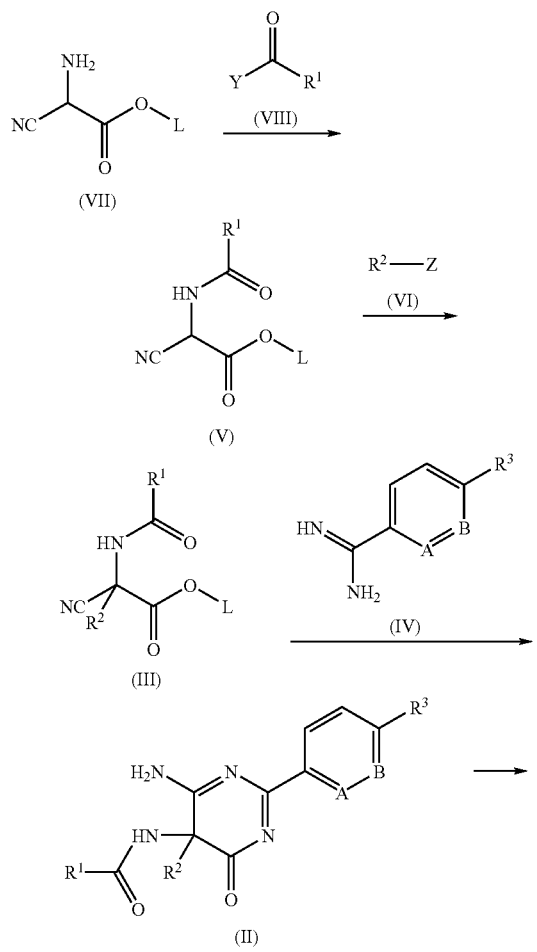

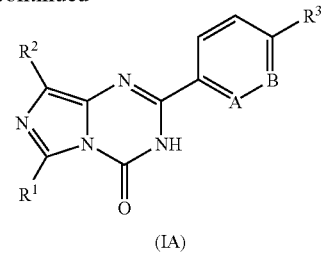

wherein, A, B, $R^1$, $R^2$ and $R^3$ have same meaning mentioned above; L is $C_1$-$C_3$ alkyl, Y is hydroxyl or a halogen atom, preferably chlorine atom, and Z is a halogen atom, preferably iodine atom.

At the beginning, to carryout the method described above, the compound (V) is obtained from the compound (VII) in accordance with the known method. This method can be conducted by the reaction of the amine compound (VII) with carboxylic acid derivatives (VIII) to obtain the corresponding acid amide compound (V) by the various methods. For example, in the case of the compound (VIII) in which Y is halogen atom, preferably chlorine atom, the reaction can be conducted by reacting the compound (VII) with 1.0 to 1.5 equivalent, preferably 1.2 equivalent of the compound (VIII) in the presence of 1 to 5 equivalent, preferably 1.5 equivalent of tertiary amine such as triethylamine, based on the compound (VII), and if necessary in the presence of the catalyst such as 4-dimethylaminopyridine.

Furthermore, in the case of the compound (VIII) in which Y is hydroxyl group, the reaction can be conducted by reacting the compound (VII) with 1.0 to 1.5 equivalent, preferably 1.2 equivalent of the compound (VIII) in the presence of 1 to 5 equivalent, preferably 1.2 equivalent of the condensing agent such as 1-ethyl-3-(3-dimethyl-aminopropyl) carbodiimide, based on the compound (VII), and if necessary in the presence of the catalyst such as 4-dimethylaminopyridine.

After the reaction is completed, the reaction mixture is diluted with the organic solvent, which is nonmiscible solvent with water, and the organic layer is washed sequentially with water and saturated saline solution, then, the solvent is removed to give the purpose compound (V). This compound can be purified by column chromatography, if necessary.

The compound (VII) to be used in this reaction can be commercially available or known compound and the compound (VIII) to be used in this reaction can also be commercially available or known compound.

Then, the compound (V) is converted to the compound (III) in accordance with the known reaction method. The reaction can be conducted by reacting the compound (V) with the compound (VI) in the presence of 1 to 1.5 equivalent, preferably 1.0 equivalent of metal alkoxide such as sodium ethoxide or sodium methoxide, based on the compound (V). The reaction can be carried out in alcohols solvent such as methanol or ethanol at 0° C. to the reflux temperature of the solvent. After the reaction is completed, the reaction mixture is acidified with inorganic acid such as hydrochloric acid, and the mixture is extracted with the organic solvent, which is nonmiscible solvent with water, and the extract is washed sequentially with water and saturated saline solution. Then, the solvent is removed to give the purpose compound (III). This compound can be purified by column chromatography, if necessary.

The obtained compound (III) is converted to the compound (II) in accordance with the known method. The reaction can be conducted by reacting the compound (III) with 0.3 to 2.0 equivalent, preferably 0.5 equivalent of the compound (IV) in alcohols solvent such as methanol or ethanol, at room temperature to the reflux temperature of the solvent. After the reaction is completed, water is added to the reaction mixture and the mixture is extracted with the organic solvent, which is nonmiscible solvent with water. The extracted organic layer is washed sequentially with water and saturated saline solution, then, the solvent is removed to give the purpose compound (II). This compound can be purified by column chromatography, if necessary.

solvent, which is nonmiscible solvent with water. The extracted organic layer is washed sequentially with water and saturated saline solution, then, the solvent is removed to give the purpose compound (IA). This compound can be purified by column chromatography, if necessary.

All reaction mentioned above are well known, and the reagents to be used or the reaction conditions to be applied can be easily established in accordance with the standard text book and the examples mentioned later. Therefore, the other methods or modified methods for obtaining the compound (IA) of the present invention can be easily selected by the person skilled in this field.

The compound of the formula (IB) of the present invention may be synthesized by the following methods.

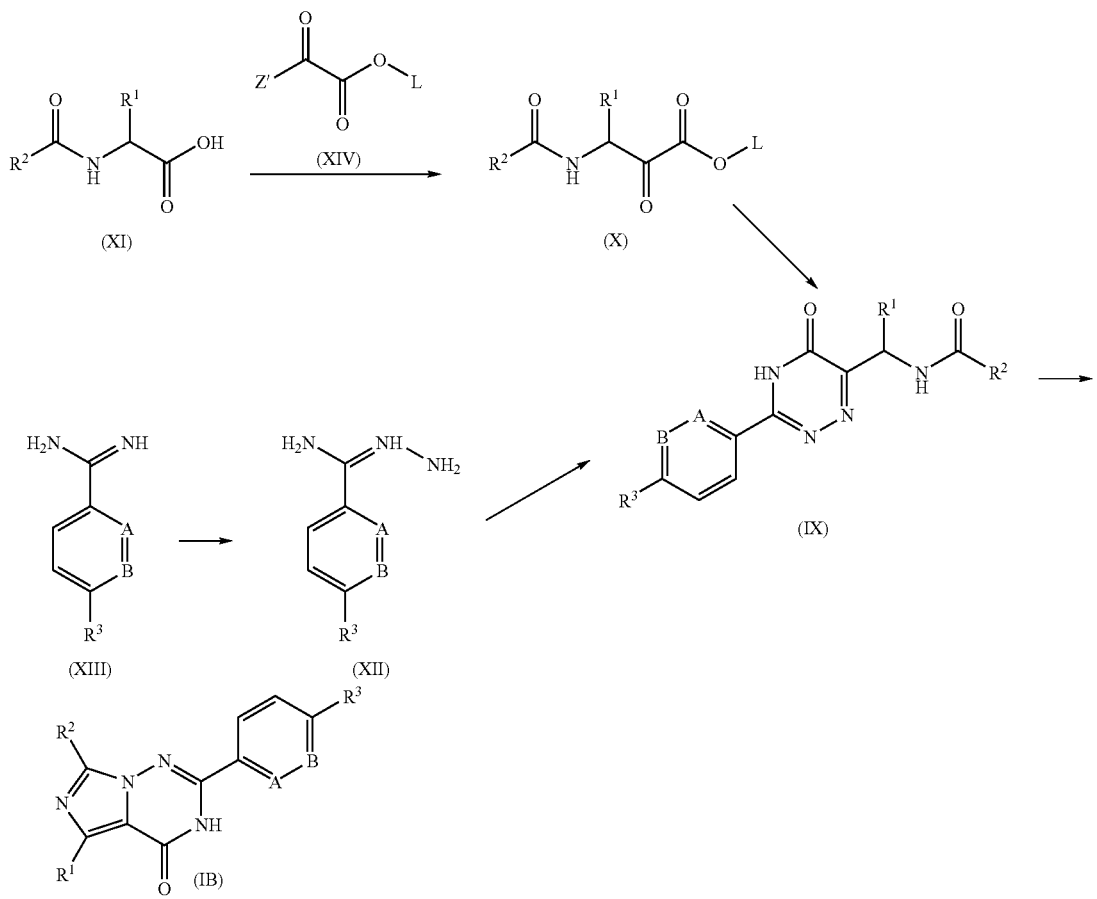

Next, the compound (IA) of the present invention can be obtained from the compound (II) by imidazotriazinone ring formation reaction. The reaction can be conducted in accordance with the known methods (e.g., *J. Org. Chem.*, 1981, 46, 3681-3685). Specifically, to pyridine solution of the compound (II) is added 1 to 5 equivalent, preferably 3 equivalent chlorotrimethylsilane and the mixture is stirred. Then, 1 to 5 equivalent, preferably 3 equivalent of hexamethyldisilazane is added to the reaction mixture, and reaction is continued at the room temperature to the reflux temperature of the solvent. After the reaction is completed, the solvent is removed and alcohols solvent such as methanol or ethanol is added to the residue and the solvent is stirred and removed. Water is added to the residue and the mixture is extracted with the organic wherein, A, B, $R^1$, $R^2$ and $R^3$ have same meaning mentioned above; L is $C_1$-$C_3$ lower alkyl, and Z' is halogen atom, preferably chlorine atom.

The compound (IB) of the present invention can be obtained in accordance with the known method (e.g., Japanese Patent Publication No. 2001-522851). That is, the compound (X) is obtained by the reaction of the compound (XI) with the compound (XIV). This reaction can be conducted in ethers solvent such as tetrahydrofuran, in the presence of organic base such as pyridine or triethylamin, and catalyst such as 4-dimethylaminopyridine, at 0° C. to reflux temperature. Separately, the compound (XII) is obtained from the compound (XIII) by reacting hydrazine hydrate in alcohols solvent at 0° C. to reflux temperature.

Then, the compound (IX) is obtained by reacting the above compound (X) with the compound (XII) in alcohols solvent such as ethanol at room temperature to reflux temperature. Finally, the purpose compound (IB) is obtained by the reaction of the compound (IX) with phosphorus oxychloride in a halogenated hydrocarbon such as 1,2-dichloromethane or chloroform.

After the reaction is completed, the solvent is neutralized by adding inorganic base aqueous solution such as sodium hydrogen carbonate aqueous solution, and the mixture is extracted with the organic solvent, which is nonmiscible solvent with water. The extracted organic layer is washed sequentially with water and saturated saline solution, then, the solvent is removed to give the purpose compound (IB).

The compounds (XI), (XIV) and (XIII) to be used in this reaction can be commercially available or known compounds. Further, the compound (XIII) to be used in this reaction can also be prepared in accordance with the known method (e.g., Japanese Patent Publication No. 2001-522851).

All reaction mentioned above are well known, and the reagents to be used or the reaction conditions to be applied can be easily established in accordance with the standard text book and the examples mentioned later. Therefore, the other methods or modified methods for obtaining the compound (IB) of the present invention can be easily selected by the person skilled in the art in this field.

EXAMPLES

The present invention is illustrated in more detail by way of the following Biological Test and Examples, but it is to be noted that, the present invention is not limited by those Examples in any way.

The synthesis of the compounds of the present invention and intermediate compounds to be used in the synthesis are illustrated in the Example mentioned later. Further, the physicochemical data and chemical structure of the compounds and intermediate compounds obtained by the Examples are summarized in the Tables mentions later.

The compound numbers in the Examples are identical to those in the Tables.

The PDE 7 (phosphodiesterase VII) inhibiting effect of the compounds of the present invention obtained in the later mentioned Examples was evaluated by mean of the following Biological Tests.

Biological Test 1

Methods for Evaluating the PDE 7 Inhibiting Effect

The PDE 7 (phosphodiesterase VII) inhibiting effect of the compounds of the present invention was performed by the following method, which was modified assay method described in *Biochemical. Pharmacol.* 48(6), 1219-1223 (1994).

(1) The active fraction of PDE 7 (phosphodiesterase VII) was obtained. That is, MOLT-4 (obtainable from ATCC as ATCC No. CRL-1582), which was cell line of human acute lymphoblastic lymphoma T cells, was incubated in RPMI1640 culture medium containing 10% fetal bovine serum to obtain $5\times10^8$ MOLT-4 cells. The cells were collected by centrifugation and suspended with 10 mL of buffer solution A [25 mM of tris-HCl, 5 mM of 2-mercaptoethnol, 2 mM of benzamidine, 2 mM of EDTA, 0.1 mM of 4-(2-aminoethyl) benzensulfonyl hydrochloride; pH 7.5], then homogenized by Polytron® homogenizer. The homogenate were centrifuged under 25,000×G for 10 minutes at 4° C. The supernatant was separated and thus obtained supernatant was further centrifuged under 100,000×G for 60 minutes at 4° C., and then filtrated with 0.2 μm filter to obtain the soluble fraction.

(2) The obtained soluble fraction was filled in equilibrium HiTrap Q column (5 mL×2) with buffer solution A, and phosphodiesterase fractions were eluted by 300 mL of buffer solution A with linear gradient from 0 to 0.8 M NaCl concentration. 5 ml each of 60 eluents were collected, and each eluents were examined for cyclic AMP metabolic activities of phosphodiesterase. The fraction eluting with about 350 mM NaCl concentration parts, where metabolic activities were not inactivated by 10 μM of rolipram (selective inhibitor for phosphodiesterase IV) and 10 μM of milrinone (selective inhibitor for phosphodiesterase III), were collected as storage solution for using to test PDE 7 inhibiting effect.

(3) The tested compound having desired concentration was reacted in the solution of 20 mM tris-HCl (pH 7.5), 1 mM of $MgCl_2$, 100 μM of EDTA, 330 μg/mL of bovine serum albumin, 4 μg/mL of 5'-nucleotidase, 0.1 μCi of $^3$H-cAMP (0.064 μM of cAMP), 10 μM of rolipram in storage solution of PDE 7 for 2 hours at 25° C. After the reaction, suspension of SEPHADEX®-QAE (cross-linked dextran gel) in 10 mM of HEPES-Na (pH 7.0) was added to the reaction mixture, and the mixture was left at rest for 5 minutes. Further, SEPHADEX®-QAE (cross-linked dextran gel) was added to the obtained supernatant and the mixture was leaved at rest for 5 minutes, then, the radioactivity of the solution was measured.

(4) $IC_{50}$ was calculated as 50% inhibiting concentration of the metabolic activities of phosphodiesterase VII of the tested compound.

The following are PDE 7 inhibiting activities of the tested compounds.

Compound 8: $IC_{50}$=0.34 μM;
Compound 11: $IC_{50}$=0.055 μM;
Compound 12: $IC_{50}$=0.49 μM:

As described above, the compounds of the present invention showed significant PDE 7 inhibiting effect.

The compounds of the present invention selectively inhibit PDE 7 and their selectivities are more than 10 times compared to PDE 4 (phosphodiesterase IV), which is similar to the PDE 7. Therefore, it is expected that the side effect of the compounds of the present invention caused by PDE4 to be less. The selectivity against PDE4 (phosphodiesterase IV) of the compounds of the present invention was affirmed by means of the following Biological Test.

Biological Test 2

Methods for Evaluating the PDE 4 Inhibiting Effect

The PDE 4 (phosphodiesterase IV) inhibiting effect of the compounds of the present invention was performed by the following method, which was modified assay method described in *Biochemical. Pharmacol.* 48(6), 1219-1223 (1994).

(1) The active fraction of PDE 4 (phosphodiesterase IV) was obtained. That is, the livers obtained from three Balb/c mice (male, 12 weeks: obtainable from CLEA Japan, Inc.) were suspended with 30 mL of buffer solution B [20 mM of bis-tris, 5 mM of 2-mercaptoethnol, 2 mM of benzamidine, 2 mM of EDTA, 0.1 mM of 4-(2-aminoethyl)benzensulfonyl hydrochloride, 50 mM of sodium acetate; pH 6.5], then homogenized by POLYTRON® homogenizer. The homogenate were centrifuged under 25,000×G for 10 minutes at 4° C. The supernatant was separated and thus obtained supernatant was further centrifuged under 100,000×G for 60 minutes at 4° C., and then filtrated with 0.2 μm filter to obtain the soluble fraction.

(2) The obtained soluble fraction was filled in equilibrium DEAE sepharose column (1×10 cm) with buffer solution B, and phosphodiesterase fractions were eluted by 120 mL of buffer solution B with linear gradient from 0.05 to 1M sodium acetate concentration. 5 ml each of 24 eluents were collected, and each eluents were examined for cyclic AMP metabolic activities of phosphodiesterase. The fraction eluting with about 620 mM of sodium acetate concentration parts, where metabolic activities were inactivated by 30 μM of rolipram (selective inhibitor for phosphodiesterase IV), were collected as storage solution to test PDE 4 inhibiting effect.

(3) The tested compound having desired concentration was reacted in the solution of 20 mM tris-HCl (pH 7.5), 1 mM of $MgCl_2$, 100 μM of EDTA, 330 μg/mL of bovine serum albumin, 4 μg/mL of 5'-nucleotidase, 0.1 μCi of $^3$H-cAMP (0.064 μM of cAMP), and storage solution of PDE 4 for 2 hours at 25° C. After the reaction, suspension of SEPHADEX®-QAE cross-linked dextran gel) in 10 mM of HEPES-Na (pH 7.0) was added to the reaction mixture, and the mixture was left at rest for 5 minutes. Further, SEPHADEX®-QAE (cross linked dextran gel) was added to the obtained supernatant and the mixture was left at rest for 5 minutes, then, the radioactivity of the solution was measured.

(4) $IC_{50}$ was calculated as 50% inhibiting concentration of the metabolic activities of phosphodiesterase IV of the tested compound.

As the results of the mentioned above Biological Test 2, the $IC_{50}$ of the compounds of the present invention was more than 10 times weaker than that of PDE 7 inhibiting effect.

The compounds of the present invention inhibit PDE 7 selectively, and therefore, enhance cellular CAMP level. Consequently, the compounds of the present invention are useful for treating various kinds of disease such as allergic disease, inflammatory disease or immunologic disease. For example, the compounds of the present invention are useful for treating or preventing the diseases such as bronchial asthma, chronic bronchitis, chronic obstructive pulmonary disease, allergic rhinitis, psoriasis, atopic dermatitis, conjunctivitis, osteoarthritis, rheumatoid arthritis, multiple sclerosis, systemic lupus erythematosus, inflammatory bowel disease, hepatitis, pancreatitis, encephalomyelitis, septicemia, Crohn's disease, rejection for organ transplantation, graft versus host disease (GVH disease), and restenosis after angioplasty.

The compounds of the present invention can be used for preparation of the pharmaceutical composition or PDE 7 inhibitor. As an active ingredient, one or more compounds may be administered in the appropriated formulation. The formulation for oral administration may include for example, capsules, granules, fine granules, syrups, dry syrups or the like; the formulation for parenteral administration may include, for example injectable solution, suppository formulation such as rectal suppository or vaginal suppository, nasal administration such as sprays, or percutaneous absorption formulation such as ointment and tapes, and the like.

The administration dose may vary depending on the various kinds of factors. These factors may be the condition of the patients, the severity of the disease, ages, existence of a complication, as well as formulation. A usual recommended daily dose for oral administration is within the range of 0.1-1,000 mg/day/adult, preferably 0.1-500 mg/day/adult, and more preferably 1-100 mg/day/adult. In the case of parenteral administration, a usual recommended daily dose is within the range of 1/1000 to 1/2 based on dose of oral administration. These doses can be adjusted depending on age, as well as the patient's condition.

The toxicological properties of the compounds of the present invention is low, therefore, the compounds of the present invention is expected to have high safety margin.

Manufacturing Examples and Examples

The synthesis of the compounds of the present invention and intermediate compounds to be used in the synthesis are illustrated in the following Manufacturing Examples and Examples.

The physicochemical data and chemical structure of the compounds are summarized in the Tables mentions later. The compound numbers in the Examples are identical to those in the Tables.

Manufacturing Example 1

Compound 1

4-Bromo-2-methoxybenzamide

To a suspension of 12.59 g (54.55 mmol) of 4-bromo-2-methoxybenzamide in 70 mL of 1,2-dichloroethane was added 11.9 mL (163.5 mmol) of thionyl chloride, and the mixture was refluxed for 2 hours. The solvent was removed under reduced pressure to obtain the corresponding acid chloride. Then, to 125 mL of 28% ammonia solution was added dripping solution of above acid chloride in 80 mL of acetone at 0° C., and the resulting precipitate was collected to give 9.22 g (74%) of the title compound.

Manufacturing Example 2

Compound 2

4-Bromo-2-methoxybenzonitrile

To a solution of 9.22 g (40.1 mmol) of the compound obtained in the Manufacturing Example 1 in 200 mL of anhydrous dichloromethane were added 11.17 mL (80.2 mmol) of triethylamine and 8.09 mL of anhydrous trifluoromethanesulfonic acid at 0° C., and the mixture was stirred for 30 minutes at the same temperature and for 1 hour at room temperature. Then, water was added to the reaction mixture and the mixture was extracted with dichloromethane. The solvent was removed under reduced pressure and the residue was purified by silica gel column chromatography (eluent: chloroform) to give 7.84 g (92%) of the title compound.

Manufacturing Example 3

Compound 3

4-Bromo-2-methoxybenzamidine hydrochloride

To a suspension of 5.349 g (100 mmol) of ammonium chloride in 200 mL of toluene was dropped 100 mL (100 mmol) of 1M-triethylaluminum/hexane, and the mixture was stirred for 1.5 hours at room temperature. Then, to this mixture was added 8.48 g (40 mmol) of the compound obtained in the Manufacturing Example 2, and the mixture was stirred for 24 hours at 80°. After the reaction mixture was cooled with ice water, 30 g of silica gel and 300 mL of chloroform were added to the mixture and the mixture was stirred for 30 minutes under the room temperature. The mixture was filtrated with Celite® and the residue was washed with 400 mL of methanol. The organic layer was concentrated and 200 mL of chloroform/methanol (9/1) solution was added to the residue. The mixture was filtrated and the filtrate was concentrated and the residue was washed sequentially with ether to give 3.47 g (33%) of the title compound.

Manufacturing Example 4

Compound 4

(R)-(Acetylamino)(cyclohexyl)acetic acid

To a solution of 15 g of (R)-(acetylamino) (1,4-cyclohexadiene-1-yl)acetic acid in 500 mL of methanol was added 500 mg of platinum oxide, and the mixture was stirred for 4 hours under hydrogen gas atmosphere. Then, the reaction mixture was filtrated and the filtrate was condensed. The residue was recrystallized from ethanol to give 11.4 g (75%) of the title compound.

Manufacturing Example 5

Compound 5

Ethyl cyano[(cyclohexylcarbonyl)amino]acetate

To a solution of 18.3 g (143 mmol) of ethyl amino(cyano)acetate in 500 mL of anhydrous dichloromethane were added 30 mL (214 mmol) of triethylamine and 23 mL (171 mmol) of cyclohexanecarbonyl chloride, and the mixture was stirred for 3 hours at 0° C. Then, saturated sodium hydrogen carbonate aqueous solution was added to the reaction mixture and the mixture was extracted with dichloromethane. The organic layer was washed with water and saturated saline solution, then, dried over with anhydrous sodium sulfate. The solvent was removed under reduced pressure and the residue was treated with ethyl acetate to give the solid substance. The obtained solid substance was collected and the filtrate was removed under reduced pressure. The obtained residue was treated with ethyl acetate to give solid substance. This treatment was further repeated. The filtrate was purified by silica gel column chromatography (eluent: dichloromethane/methanol=50/1) to give crude crystalline. The obtained crude crystalline was washed with ether and combined with the above all solid products to give 24.3 g (71%) of the title compound.

Manufacturing Example 6

Compound 6

Ethyl 2-cyano-2-[(cyclohexylcarbonyl)amino]propanoate

Sodium ethoxide was prepared from 2.3 g (102 mmol) of sodium and 150 mL of ethanol, and to this mixture was added a suspension of 24.2 g (102 mmol) of the compound obtained in the Manufacturing Example 5 in 150 mL of ethanol at 0° C., and then, the mixture was stirred through the suspension was perfectly dissolved. Then, 6.32 mL (102 mmol) of methyl iodide was added to the reaction mixture after stirring 4 hours at room temperature, the reaction mixture was acidified with 1M-HCl, then, the solvent was removed under reduced pressure. Water was added to the residue and the mixture was extracted with dichloromethane. Then the organic layer was washed with saturated saline solution and dried over with anhydrous sodium sulfate. The solvent was removed under reduced pressure and the residue was treated with a mixture solvent of ethyl acetate/hexane (1/1) to give the solid substance. The obtained solid substance was collected by the filtration and the filtrate was removed under reduced pressure. The residue was further treated with a mixture solvent of ethyl acetate/hexane (1/1) to give the solid substance. The obtained solid substance was collected by the filtration and the filtrate was purified by silica gel column chromatography (eluent: hexane/ethyl acetate=2/1), and the obtained solid substance was combined with the above solid substances to give 22.8 g (88%) of the title compound.

Manufacturing Example 7

Compound 7

N-[6-Amino-2-(2-methoxyphenyl)-5-methyl-4-oxo-4,5-dihydro-5-pyrimidinyl]cyclohexanecarboxamide Sodium ethoxide was prepared from 117 mg (5.10 mmol) of sodium and 16 mL of ethanol, and to this mixture was added 865 mg (4.64 mmol) of 2-methoxybenzamidine hydrochloride, then, the mixture was stirred for 45 minutes at room temperature. The unsolved substance was removed off by filtration and 2.34 g (9.27 mmol) of the compound obtained in the Manufacturing Example 6 in 25 mL of methanol solution was added to the filtrate, and the mixture was refluxed for 20 hours. After the reaction mixture was cooled to the room temperature, appeared precipitate was collected by the filtration. The filtrate was removed under reduced pressure and water was added to the residue, then, the mixture was extracted with dichloromethane. The organic layer was washed with water and saturated saline solution, then, dried over with anhydrous sodium sulfate. The solvent was removed under reduced pressure and the residue was combined with above obtained precipitate, then, recrystallized from ethanol to give the solid. The filtrate was purified by silica gel column chromatography (eluent: dichloromethane/methanol=20/1 to 10/1) to give the solid substance, and this solid substance was combined with above obtained solid substance to give 343 mg (21%) of the title compound.

Example 1

Compound 8

6-Cyclohexyl-2-(2-methoxyphenyl)-8-methylimidazo[1,5-a][1,3,5]-triazin-4(3H)-one To a suspension of 320 mg (0.90 mmol) of the compound obtained in the Manufacturing Example 7 in 15 mL of pyridine was added 0.34 mL (2.7 mmol) of chlorotrimethylsilane, and the mixture was stirred for 30 minutes at room temperature. Then, 0.57 mL (2.7 mmol) of hexamethyldisilazane was added to the reaction mixture and the mixture was refluxed for 5 hours. After the reaction mixture was cooled to the room temperature, the solvent was removed under reduced pressure and methanol was added to the residue, then, the mixture was stirred for 1 hour. The solvent was removed under reduced pressure and the residue was purified by silica gel column chromatography (eluent: hexane/ethyl acetate=1/1) to give 20 mg (7%) of the title compound.

Manufacturing Example 8

Compound 9

N-[6-Amino-2-(4-bromo-2-methoxyphenyl)-5-methyl-4-oxo-4,5-dihydro-5-pyrimidinyl]cyclohexanecarboxamide The title compound 439 mg (9%) was obtained in a manner similar to the Manufacturing Example 7 by using the compound obtained in the Manufacturing Example 3 instead of 2-methoxybenzamidine hydrochloride.

Example 2

Compound 10

2-(4-Bromo-2-methoxyphenyl)-6-cyclohexyl-8-methylimidazo-[1,5-a][1,3,5]triazin-4(3H)-one The title compound 14 mg (3%) was obtained in a manner similar to the Example 1 by using the compound obtained in the Manufacturing Example 9 instead of the compound obtained in the Manufacturing Example 7.

Example 3

Compound 11

6-Cyclohexyl-2-[2-methoxy-4-(4-methyl-1-piperadinyl)phenyl]-8-methylimidazo[1,5-a][1,3,5]triazin-4(3H)-one To a solution of 12 mg (0.029 mmol) of the compound obtained in the Example 2 in 2 mL of toluene were added 5.5 mg (0.058 mmol) of sodium tert-butoxide, 0.6 mg (0.0029 mmol) of tri-tert-butylphosphine and 0.3 mg (0.0014 mmol) of palladium(II) acetate under argon gas atmosphere, and the mixture was stirred for 4 hours at 110° C. After the reaction mixture was cooled to the room temperature, water was added to the mixture and the mixture was extracted with ethyl acetate. The organic layer was washed with water and saturated saline solution, and dried over with anhydrous sodium sulfate. The solvent was removed under reduced pressure and the residue was purified by silica gel column chromatography (eluent: dichloromethane/methanol=30/1 to 10/1) to give 3 mg (24%) of the title compound.

Example 4

Compound 12

5-Cyclohexyl-2-(2-methoxyphenyl)-7-methylimidazo-[5,1-f][1,2,4]triazin-4(3H)-one To a solution of 1.5 g (7.52 mmol) of the compound obtained in the Manufacturing Example 4 in 5 mL of pyridine was added ca. 5 mg of DMAP, and the mixture was refluxed. Then, 1.68 mL (15.06 mmol) of ethyl oxalyl chloride was added by dripping to this mixture and the mixture was refluxed for 3 hours. The reaction mixture was poured into ice water and extracted with ethyl acetate. The extract was dried over with anhydrous sodium sulfate and removed under reduced pressure. The residue was dissolved in 5 mL of ethanol and the mixture was refluxed for 2.5 hours with sodium hydrogen carbonate, then, filtrated after cooling to give ethanol filtrate. Next, 365 μL (7.52 mmol) of hydrazine hydrate was added by dripping to a solution of 1.41 g (7.32 mmol) of 2-methoxybenzamidine hydrochloride in 8 mL of ethanol, and the mixture was stirred for 10 minutes at the room temperature. Then, to this mixture was added above obtained ethanol filtrate, and the mixture was stirred for 4 hours at 70° C. After the reaction, the mixture was filtrated and the filtrate was diluted with dichloromethane. The organic layer was washed with water and dried over with anhydrous sodium sulfate. The solvent was removed under reduced pressure and the residue was dissolved into 10 mL of 1,2-dichloromethane, then, 1.25 mL of phosphorus oxychloride was added. After the mixture was refluxed for 2 hours, the reaction mixture was cooled to the room temperature, and diluted with dichloromethane, then neutralized with saturated sodium hydrogen carbonate and solid sodium hydrogen carbonate. The organic layer was separated and dried over with anhydrous sodium sulfate. The solvent was removed under reduced pressure and the residue was purified by silica gel column chromatography to give 5 mg (0.2%) of the title compound.

Physicochemical data and chemical structure of the compounds obtained by the above-mentioned examples are summarized in the following Tables.

TABLE 1

| Comp. No. | Chemical Structure | Properties m.p. (° C.) (recryst. solvent) | $^1$H-NMR | MS (ESI) (M + 1)$^+$ |
|---|---|---|---|---|
| 1 | (structure: 4-Br, 2-OMe benzamide) | pale yellow solid 138-139 | CDCl$_3$ 3.97 (3H, s), 5.74 (1H, brs), 7.13 (1H, d, J=1.6Hz), 7.22 (1H, dd, J=1.6 and 9.3Hz), 7.57 (1H, brs), 8.06 (1H, d, J=9.3Hz) | 230 |

TABLE 1-continued

| Comp. No. | Chemical Structure | Properties m.p. (° C.) (recryst. solvent) | ¹H-NMR | MS (ESI) $(M + 1)^+$ |
|---|---|---|---|---|
| 2 | (4-bromo-2-methoxybenzonitrile) | pale yellow solid 134-137 | CDCl$_3$ 3.93 (3H, s), 7.12 (1H, d, J=1.7Hz), 7.16 (1H, dd, J=1.7 and 8.2Hz), 7.40 (1H, d, J=8.2Hz) | 212 |
| 3 | (4-bromo-2-methoxybenzamidine HCl) | colorless solid 230 (dec.) | DMSO-d$_6$ 3.89 (3H, s), 7.33-7.37 (1H, m), 7.44-7.51 (2H, m), 9.04 (3H, brs) | 229 |
| 4 | (N-acetyl cyclohexylglycine) | colorless solid 215-216 (EtOH) | CDCl$_3$ 0.92-1.26 (5H, m), 1.50-1.70 (6H, m), 1.83 (3H, s), 4.08 (1H, dd, J=6.2 and 8.4Hz), 7.93 (1H, dd, J=8.4Hz), 12.45 (1H, brs) | 200 |

TABLE 2

| Comp. No. | Chemical Structure | Properties m.p. (° C.) (recryst. solvent) | ¹H-NMR | MS (ESI) $(M + 1)^+$ |
|---|---|---|---|---|
| 5 | 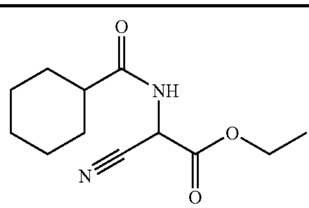 | colorless solid 141-144 | CDCl$_3$ 1.15-1.52 (5H, m), 1.35 (3H, t, J=7.1Hz), 1.63-1.71 (1H, m), 1.73-1.93 (4H, m), 2.17-2.27 (1H, m), 4.34 (2H, q, J=7.1Hz), 5.52 (1H, d, J=7.7Hz), 6.25 (1H, brd, J=7.7Hz) | 239 |
| 6 | 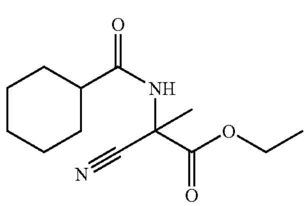 | colorless solid 114.5-116 | CDCl$_3$ 1.14-1.30 (3H, m), 1.34 (3H, t, J=7.1Hz), 1.39-1.52 (2H, m), 1.60-1.70 (1H, m), 1.75-1.92 (4H, m), 1.85 (3H, s), 2.11-2.21 (1H, m), 4.32 (2H, d, J=7.1Hz), 6.13 (1H, brs) | 253 |
| 7 | 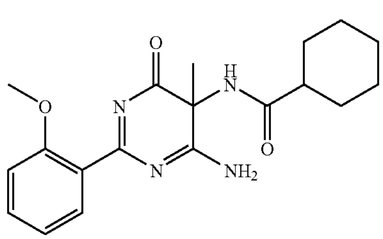 | pale yellow solid 192-195 (EtOH/H$_2$O) | CDCl$_3$ 1.13-1.33 (3H, m), 1.39-1.87 (5H, m), 1.70 (3H, s), 1.89-2.00 (2H, m), 2.18-2.29 (1H, m), 3.99 (3H, s), 6.38 (1H, brs), 6.97-7.04 (1H, m), 7.08-7.15 (1H, m), 7.49-7.59 (1H, m), 8.36-8.48 (1H, m), | 357 |

TABLE 2-continued

| Comp. No. | Chemical Structure | Properties m.p. (° C.) (recryst. solvent) | ¹H-NMR | MS (ESI) (M + 1)⁺ |
|---|---|---|---|---|
| 8 | 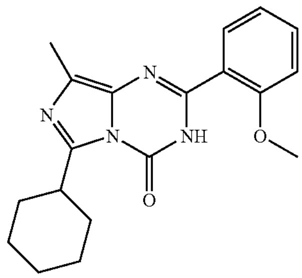 | pale yellow solid 228-230 | CDCl₃ 1.20-1.35 (1H, m), 1.39-1.76 (5H, m), 1.79-1.90 (2H, m), 2.01-2.11 (2H, m), 2.44 (3H, s), 3.54-3.67 (1H, m), 4.03 (3H, s), 7.00-7.07 (1H, m), 7.10-7.17 (1H, m), 7.43-7.51 (1H, m), 8.36-8.41 (1H, m), 10.03 (1H, brs) | 339 |

TABLE 3

| Comp. No. | Chemical Structure | Properties m.p. (° C.) (recryst. solvent) | ¹H-NMR | MS (ESI) (M + 1)⁺ |
|---|---|---|---|---|
| 9 | 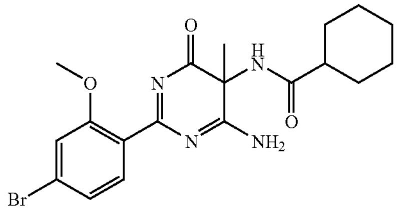 | pale yellow solid 190-192 | DMSO-d₆ 1.05-1.29 (5H, m), 1.40 (3H, s), 1.53-1.82 (5H, m), 2.18-2.28 (1H, m), 3.78 (3H, s), 7.12-19 (1H, m), 7.21-7.28 (1H, m), 7.39-7.49 (1H, m), 8.62 (1H, brs) | 435 |
| 10 | 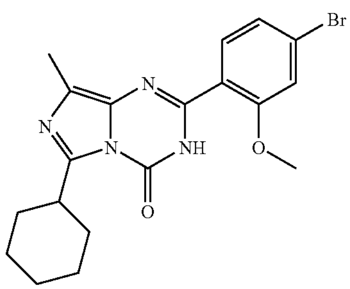 | pale yellow solid 143-146 | CDCl₃ 1.21-1.34 (1H, m), 1.38-1.77 (5H, m), 1.79-1.89 (2H, m), 2.01-2.10 (2H, m), 2.42 (3H, s), 3.53-3.66 (1H, m), 4.03 (3H, s), 7.18 (1H, d, J=1.6Hz), 7.27 (1H, dd, J=1.6 and 8.6Hz), 8.25 (1H, d, J=8.6Hz), 9.84 (1H, brs) | 417 |
| 11 | 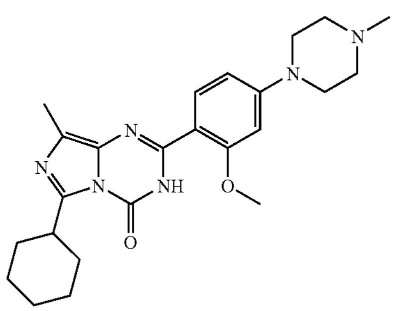 | pale yellow solid 184-189.5 | CDCl₃ 1.21-1.77 (6H, m), 1.80-1.89 (2H, m), 2.01-2.11 (2H, m), 2.36 (3H, s), 2.41 (3H, s), 2.51-2.61 (4H, m), 3.32-3.40 (4H, m), 3.54-3.68 (1H, m), 4.00 (3H, s), 6.40 (1H, d, J=2.1Hz), 6.62 (1H, dd, J=2.1 and 9.0Hz), 8.25 (1H, d, J=9.0Hz), 10.02 (1H, brs) | 437 |
| 12 | 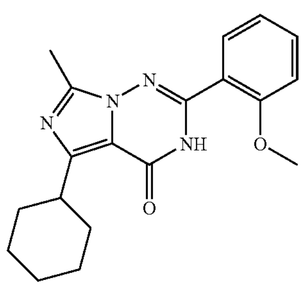 | pale yellow solid | CDCl₃ 1.15-1.93 (10H, m), 2.64 (3H, s), 3.24-3.34 (1H, m), 4.00 (3H, s), 7.04-7.08 (1H, m), 7.11-7.16 (1H, m), 7.48-7.55 (1H, m), 8.13-8.18 (1H, m), 9.65 (1H, brs) | 339 |

INDUSTRIAL APPLICABILITY

The compounds of the present invention inhibit PDE 7 selectively, and therefore, enhance cellular CAMP level. Consequently, the compounds of the present invention are useful for treating various kinds of disease such as allergic disease, inflammatory disease or immunologic disease.

That is, the compounds of the present invention are useful for preventing or treating the diseases such as bronchial asthma, chronic bronchitis, chronic obstructive pulmonary disease, allergic rhinitis, psoriasis, atopic dermatitis, conjunctivitis, osteoarthritis, rheumatoid arthritis, multiple sclerosis, systemic lupus erythematosus, inflammatory bowel disease, hepatitis, pancreatitis, encephalomyelitis, septicemia, Crohn's disease, rejection for organ transplantation, GVH disease, and restenosis after angioplasty.

The invention claimed is:

1. A compound represented by the following formula (IA):

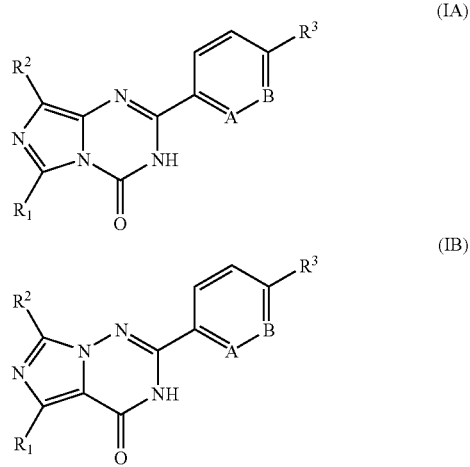

wherein
A is N or $CR^4$;
B is N or CH;
$R^1$ is substituted or unsubstituted cycloalkyl group or tert-butyl group;
$R^2$ is a hydrogen atom or $C_1$-$C_6$ alkyl group;
$R^3$ is a hydrogen atom; intro group; cyano group; a halogen atom; heteroaryl group, wherein the heteroaryl group is pyrrole, furyl, thienyl, imidazolyl, thiazolyl, pyrazinyl, indolyl, quinolinyl, isoquinolinyl, tetrazolyl, pyridinyl, pyrazolyl, pyridazinyl, or pyrimidinyl; substituted or unsubstituted $C_1$-$C_6$ alkyl group; substituted or unsubstituted $C_2$-$C_6$ alkenyl group; saturated or unsaturated heterocycloalkyl group which is substituted or unsubstituted; a group: —$NR^5R^6$, —$C(O)R^7$, —$SO_2R^7$, —$OR^8$, —$NR^8COR^7$, —$NR^8SO_2R^7$;
$R^4$ is a hydrogen atom or $C_1$-$C_3$ alkoxy group which is unsubstituted or substituted by one or more fluorine atom(s);
$R^5$ and $R^6$ are, same or different from each other, a hydrogen atom; substituted or unsubstituted $C_1$-$C_6$ alkyl group; substituted or unsubstituted acyl group; or substituted or unsubstituted heterocycloalkyl group;
$R^7$ is a hydrogen atom; substituted or unsubstituted $C_1$-$C_6$ alkyl group; substituted or unsubstituted heterocycloalkyl group; OH; —$OR^8$ or —$NR^5R^6$;
$R^8$ is a hydrogen atom, substituted or unsubstituted $C_1$-$C_6$ alkyl group; or substituted or unsubstituted heterocycloalkyl group; or pharmaceutically acceptable salts thereof.

2. The compound according to claim 1, in which $R^1$ is substituted or unsubstituted $C_3$-$C_8$ cycloalkyl group.

3. The compound according to claim 2, in which $R^1$ is cyclopentyl, cyclohexyl or cycloheptyl.

4. The compound according to claim 1, in which A is $CR^4$ wherein $R^4$ is methoxy or ethoxy group.

5. The compound according to claim 1, in which B is CH.

6. The compound according to claim 1, in which $R^2$ is methyl group.

7. The compound according to claim 1, in which $R^3$ is a hydrogen atom; a halogen atom; saturated or unsaturated heterocycloalkyl group; an —$NR^5R^6$, —$C(O)R^7$, or —$SO_2R^7$ group, wherein $R^7$ is OH, —$OR^8$, —$NR^5R^6$ or a substituted or unsubstituted heterocycloalkyl group.

8. A pharmaceutical composition comprising a compound according to claim 1, or pharmaceutically acceptable salts thereof as an active ingredient.

9. The compound of claim 1, wherein the compound is 6-cyclohexyl-2-(2-methoxyphenyl)-8-methylimidazo-[1,5-a][1,3,5]-triazin-4(3H)-one; or 6-cyclohexyl-2-(4-bromo-2-methoxyphenyl)-8-methylimidazo-[1,5-a][1,3,5]triazin-4(3H)-one.

10. The compound of claim 1, wherein the compound is 6-cyclohexyl-2-[2-methoxy-4-(1-piperazinyl)phenyl]-8-methylimidazo-[1,5-a][1,3,5]triazin-4(3H)-one; or 6-cyclohexyl-2-[2-methoxy-4-(4-methyl-1-piperazinyl)phenyl]-8-methylimidazo-[1,5-a][1,3,5]triazin-4(3H)-one.

11. The compound of claim 1, wherein the compound is 2-[4-(4-amino-1-piperidinyl)-2-methoxyphenyl]-6-cyclohexyl-8-methylimidazo[1,5-a][1,3,5]-triazin-4(3H)-one; 6-cyclohexyl-2-{2-methoxy-4-[4-(methylamino)-1-piperidinyl]phenyl}-8-methylimidazo[1,5-a][1,3,5]triazin-4(3H)-one; 6-cyclohexyl-2-{4-[4-(dimethylamino)-1-piperidinyl]-2-methoxy-phenyl}-8-methylimidazo[1,5-a][1,3,5]triazin-4(3H)-one; or 6-cyclohexyl-2-[4-(4-hydroxy-1-piperidinyl)-2-methoxyphenyl]-8-methylimidazo[1,5-a])[1,3,5]triazin-4(3H)-one.

12. The compound of claim 1, wherein the compound is 6-cyclohexyl-2-[4-(1,4-diazepan-1-yl)-2-methoxyphenyl]-8-methylimidazo[1,5-a][1,3,5]triazin-4(3H)-one; or 6-cyclohexyl-2-[2-methoxy-4-(4-methyl-1,4-diazepan-1-yl)phenyl]-8-methylimidazo[1,5-a][1,3,5]triazin-4(3H)-one.

13. The compound of claim 1, wherein the compound is 6-cyclohexyl-2-{4-[(4-hydroxy-1-piperidinyl)sulfonyl]-2-methoxyphenyl}-8-methylimidazo[1,5-a][1,3,5]triazin-4(3H)-one; 6-cyclohexyl-2-[2-methoxy-4-(1-piperazinylsulfonyl)phenyl]-8-methylimidazo[1,5-a][1,3,5]triazin-4(3H)-one; 6-cyclohexyl-2-{2-methoxy-4-[(4-methyl-1-piperazinyl)sulfonyl]phenyl}-8-methylimidazo[1,5-a][1,3,5]triazin-4(3H)-one; 6-cyclohexyl-2-[4-(1,4-diazepan-1-ylsulfonyl)-2-methoxyphenyl]-8-methylimidazo[1,5-a][1,3,5]triazin-4(3H)-one; or 6-cyclohexyl-2-{2-methoxy-4-[(4-methyl-1,4-diazepam-1-yl)sulfonyl]phenyl}-8-methylimidazo[1,5-a][1,3,5]triazin-4(3H)-one.

14. The compound of claim 13, wherein the compound is 6-cyclohexyl 2-{4-[(4-hydroxy-1-piperidinyl)sulfonyl]-2-methoxyphenyl}-8-methylimidazo[1,5-a][1,3,5]triazin-4(3H)-one.

15. The compound of claim 13, wherein the compound is 6-cyclohexyl-2-[2-methoxy-4-(1-piperazinylsulfonyl)phenyl]-8-methylimidazo[1,5-a][1,3,5]triazin-4(3H)-one; or 6-cyclohexyl-2-{2-methoxy-4-[(4-methyl-1-piperazinyl) sulfonyl]-phenyl}-8-methylimidazo[1,5-a][1,3,5]triazin-4 (3H)-one.

16. The compound of claim 13, wherein the compound is 6-cyclohexyl-2-[4-(1,4-diazepan-1-ylsulfonyl)-2-methoxyphenyl]-8-methylimidazo[1,5-a][1,3,5]triazin-4(3H)-one; or 6-cyclohexyl-2-{2-methoxy-4-[(4-methyl-1,4-diazepam-1-yl)sulfonyl]-phenyl}-8-methylimidazo[1,5-a][1,3,5]triazin-4(3H)-one.

17. The compound of claim 1, wherein the compound is 6-cyclohexyl-2-(2-ethoxyphenyl)-8-methylimidazo[1,5-a][1,3,5]-triazin-4(3H)-one.

18. The compound of claim 1, wherein the compound is 6-cyclohexyl-2-[2-ethoxy-4-(1-piperazinyl)phenyl]-8-methylimidazo[1,5-a][1,3,5]triazin-4(3H)-one; or 6-cyclohexyl-2-[2-ethoxy-4-(4-methyl-1-piperazinyl)phenyl]-8-methylimidazo[1,5-a][1,3,5]triazin-4(3H)-one.

19. The compound of claim 1, wherein the compound is 2-[4-(4-amino-1-piperidinyl)-2-ethoxyphenyl]-6-cyclohexyl-8-methylimidazo[1,5-a][1,3,5]triazin-4(3H)-one; 6-cyclohexyl-2-{2-ethoxy[4-(methylamino)-1-piperidinyl] phenyl}-8-methylimidazo[1,5-a][1,3,5]triazin-4(3H)-one; 6-cyclohexyl-2-{4-[4-(dimethylamino)-1-piperidinyl]-2-ethoxy-phenyl}-8-methylimidazo[1,5-a]([1,3,5]triazin-4 (3H)-one; or 6-cyclohexyl-2-[4-(4-hydroxy-1-piperidinyl)-2-ethoxyphenyl]-8-methylimidazo[1,5-a][1,3,5]triazin-4 (3H)-one.

20. The compound of claim 1, wherein the compound is 6-cyclohexyl-2-[4-(1,4-diazepan-1-yl)-2-ethoxyphenyl]-8-methylimidazo[1,5-a][1,3,5]triazin-4(3H)-one; or 6-cyclohexyl-2-[2-ethoxy-4-(4-methyl-1,4-diazepan-1-yl)phenyl]-8-methylimidazo[1,5-a][1,3,5]triazin-4(3H)-one.

21. The compound of claim 1, wherein the compound is 6-cyclohexyl-2-{4-[(4-hydroxy-1-piperidinyl)sulfonyl]-2-ethoxy-phenyl}-8-methylimidazo[1,5-a][1,3,5]triazin-4 (3H)-one; 6-cyclohexyl-2-[2-ethoxy-4-(1-piperazinylsulfonyl)phenyl]-8-methylimidazo[1,5-a][1,3,5]triazin-4(3H)-one; 6-cyclohexyl-2-{2-ethoxy-4-[(4-methyl-1-piperazinyl) sulfonyl]-phenyl}-8-methylimidazo[1,5-a][1,3,5]triazin-4 (3H)-one; 6-cyclohexyl-2-[4-(1,4-diazepan-1-ylsulfonyl)-2-ethoxyphenyl]-8-methylimidazo[1,5-a][1,3,5]triazin-4(3H)-one; or 6-cyclohexyl-2-{2-ethoxy-4-[(4-methyl-1,4-diazepan-1-yl)sulfonyl]-phenyl}-8-methylimidazo[1,5-a][1,3,5]triazin-4(3H)-one.

22. The compound of claim 21, wherein the compound is 6-cyclohexyl-2-{4-[(4-hydroxy-1-piperidinyl)sulfonyl]-2-ethoxy-phenyl}-8-methylimidazo[1,5-a][1,3,5]triazin-4 (3H)-one.

23. The compound of claim 21, wherein the compound is 6-cyclohexyl-2-[2-ethoxy-4-(1-piperazinylsulfonyl)phenyl]-8-methylimidazo[1,5-a][1,3,5]triazin-4(3H)-one; or 6-cyclohexyl-2-{2-ethoxyl-4-[(4-methyl-1-piperazinyl)sulfonyl]-phenyl}-8-methylimidazo[1,5-a][1,3,5]triazin-4 (3H)-one.

24. The compound of claim 21, wherein the compound is 6-cyclohexyl-2-[4-(1,4-diazepan-1-ylsulfonyl)-2-ethoxyphenyl]-8-methylimidazo[1,5-a][1,3,5]triazin-4(3H)-one; or 6-cyclohexyl-2-{2-ethoxy-4-[(4-methyl-1,4-diazepan-1-yl)sulfonyl]-phenyl}-8-methylimidazo[1,5-a][1,3,5]triazin-4(3H)-one.

* * * * *